United States Patent [19]

Bennett et al.

[11] 4,229,408

[45] Oct. 21, 1980

[54] METHOD AND COMPOSITION FOR TOILET HOLDING TANK

[75] Inventors: James D. Bennett, Arlington; Jimmy R. Coolidge; Clifford E. Murphy, both of Fort Worth, all of Tex.

[73] Assignee: CBM Enterprises, Inc., Arlington, Tex.

[21] Appl. No.: 34,608

[22] Filed: Apr. 30, 1979

[51] Int. Cl.$^2$ .................. A61L 13/02; A61L 1/00; A61L 13/00

[52] U.S. Cl. ................................ 422/5; 210/755; 210/764; 422/36; 422/37; 424/329; 424/334

[58] Field of Search ............. 422/5, 36, 37; 210/62, 210/64; 424/329, 334

[56] References Cited

U.S. PATENT DOCUMENTS

| | | | |
|---|---|---|---|
| 2,998,390 | 8/1961 | Hamilton | 422/5 X |
| 3,208,936 | 9/1965 | Hamilton | 422/5 X |
| 3,749,672 | 7/1973 | Golton et al. | 210/62 X |
| 3,881,008 | 4/1975 | Shema et al. | 210/64 X |
| 3,883,303 | 5/1975 | Roberts | 422/5 |
| 3,934,025 | 1/1976 | Swered et al. | 424/329 X |
| 3,941,696 | 3/1976 | Melnick et al. | 210/62 |
| 4,043,911 | 8/1977 | Melnick et al. | 210/62 |
| 4,107,312 | 8/1978 | Wegner et al. | 424/334 X |
| 4,125,628 | 11/1978 | Goldhaft et al. | 424/334 X |

*Primary Examiner*—Barry S. Richman
*Attorney, Agent, or Firm*—Wofford, Fails & Zobal

[57] ABSTRACT

A method and composition for controlling odor emission from toilet holding tanks for prolonged intervals of at least 48 hours consisting essentially of adding to the toilet holding tank an effective amount of an additive composition consisting essentially of a quaternary compound selected from the class consisting of alkyl dimethyl benzyl ammonium chloride and alkyl diethyl benzyl ammonium chloride where the alkyl group contains 12-18 carbon atoms, inclusive; formaldehyde; and an acid buffer sufficient to buffer the composition in the toilet system to a pH in the range of 4-5. The effective amount is that which is sufficient to maintain a concentration of at least 100 parts per million of the additive composition throughout the prolonged interval.

11 Claims, No Drawings

METHOD AND COMPOSITION FOR TOILET HOLDING TANK

BACKGROUND OF THE INVENTION

1. Field of the Invention

This invention pertains to disposal of human wastes in toilet systems in which the system has to be maintained in a toilet holding tank for a prolonged interval. In particular, this invention pertains to the disposal of human waste in situations; such as, portable toilets, vehicles like aircraft, buses, trailers, boats and the like, having chemical toilets where it is impractical or proscribed to jettison the waste material in a short time interval.

2. Description of the Prior Art

The prior art has seen a wide variety of different approaches to the treatment of human wastes or the like in chemical depositories over protracted intervals. The systems that have been developed for the prior art have been satisfactory for a short interval of time in alleviating problem with bacterial growth and odor. Recent developments in transportation and in city codes and the like have precluded the random discharge of waste materials, particularly where the additives contained toxic and non-biodegradable material such as heavy metal products. Typical of the prior art approaches are the following U.S. Pat. Nos. 3,653,499 relates to a storable stable paraformaldehyde sterilizing composition including a metal tripolyphosphate and a pH between 10 and 11, as well as other ingredients. 4,043,911, describes sterilization of holding tanks and like by quaternary compounds at a pH of 9-11 or higher. 3,883,303, describes the method for controlling odors in recirculating toilets by including in the toilet a composition containing borax and paraformaldehyde in the amount of 100-5000 parts per million. 3,208,936 describes an antiseptic recirculating toilet composition employing water, isopropanol solution, of quaternary amine such as 60 percent isopropanol solution of 1-(2-hydroxy-ethyl) 2-n-alkyl-lbenzyl-2-imidazolinium chloride in which the alkyl group is either oleic acid, 29-54 linoleic acid and 46-61 percent oleic acid mixture or stripped coco fatty acids along with amyriad of other compositions; including an acid selected from acetic and lactic to buffer the composition to a pH of approximately 5, formaldehyde, Methyl Violet and Alizarin Blue Sapphire G dye, stabilizing agent, an indicating dye selected from a group betal methyl umbelliferone and soluble fluorescein, disodium phosphate and an odor masking agent, such as cashmere oil or musk oil. 2,998,390 describes a recirculating toilet sump fluid in which quaternary ammonium salts such as p-diisobutyl phenoxy ethoxy ethyl dimethyl benzyl ammonium chloride monohydrate is employed in conjunction with boric acid and the like to buffer the material to a pH of about 5 to prevent precipitation. 4,022,911 describes a disinfectant composition comprising a quaternary ammonium compound, a phenol and formaldehyde for killing bacteria. 3,941,696 describes sterilization of holding tanks by quaternary compounds at a pH of 9-11 or higher. 4,010,277 describes a synergistic composition containing polyoxyethylene sorbitol hexaoleate having about 40 oxy-ethylene groups for controlling growth of slime in cooling water systems and effluent water treatment. 3,892,846 describes an animal bedding material treated with hydroxamic acid or salt thereof to prevent the decomposition of urea and malodor accompanying such. 4,007,262 describes an odor control system for use in a chemical toilet in which a neutral or basic transition metal salt of an inorganic acid or a lower aliphatic organic monocarboxylic acid is dissolved in aqueous ammonia or aqueous solution of a strong water soluble organic amine that is subsequentially acidified with sufficient mono- or poly-functional carboxylate acid or other suitable acidic ligand to produce a transition coordination compound and buffer system having a pH in the range of about 6.5 to 7. 3,749,672 describes a stabilized solution of N-halo compounds in which stability is provided by the inclusion of a buffer to neutralize the effects of hypobromite, hypochlorite, or hypoiodite. 3,734,291 describes waste treatment systems in which a macerator macerates the waste and provides mechanical entrapment, as by filtration. 2,990,266 describes a method for controlling plant growth in which substantially equal molar portions of a lower mono-alkanolamine and paraformaldehyde are present in combination with benzene. 3,903,259 describes a method of deodorizing diapers and human excretia with a chemical composition comprising an acidic material, antibacterial material, and a solvent selected from a specific group. 4,034,078 describes a synergistically effective composition of an enzyme such as protolytic enzyme and a ferrous salt composition. 3,881,008 describes a process for controlling slime with N-2-nitrobutyl-morpholine and N-alkyl-dimethyl-benzyl ammonium chloride.

3,459,852 describes a deodorizing treatment of aqueous solution comprising mixing a sulfide-active alpha, beta unsaturated aldehyde or ketone in an amount sufficient to form a sulfur-containing reaction product. 3,785,971 describes a waste treatment material for preserving refuse and waste material within a container comprising a mixture of paraformaldehyde, an alkali material, a masking agent, a colorant and a wetting agent. 3,350,652 describes the use of anti-microbial composition including silver, sodium hypochlorite, hydrogen peroxide and formaldehyde.

More recently, environmental protection agencies of the federal government and the like specify where discharging of waste materials is permissable and where discharging is proscribed. Compliance with these regulations often requires holding waste materials for a much longer period; for example, forty-eight hours or more; than heretofore was necessary. This extends the need for treatment and particularly odor control. This is true not only of buses, airplanes, boats, and the like, but also of recreational vehicles.

Several designs of toilet systems are in use today, but each incorporates a type of holding tank where solid wastes reside. In the holding tank is where the odors must be suppressed. In order to accomplish this goal, a deodorant additive should perform certain activities. It must subdue bacterial growth. It must destroy odors emanating from newly received waste. It must contain in solution offensive gases generated during the degradation of organic matter.

The prior art systems buffering to a pH of 5 and above have frequently killed bacteria for periods of up to twenty-four hours; but they fail in providing odor control for periods of forty-eight hours or longer.

SUMMARY OF THE INVENTION

Accordingly, it is an object of this invention to provide method and composition which can control odors in toilet systems and toilet holding tanks for a prolonged interval of forty-eight hours and more.

It is a specific object of this invention to provide a method of treating a toilet holding tank by depositing thereinto in a batch-type operation an effective amount of an additive composition that controls bacterial growth sufficiently and reduces objectionable offensive odors from the toilet holding tank for prolonged intervals of forty-eight hours or more.

It is also an object of this invention to provide an additive composition in predetermined discreet quantities such that when added to predetermined sized toilet holding tanks, objectionable odor emission is controlled for prolonged intervals of forty-eight hours and more.

These and other objects will become apparent from the descriptive matter hereinafter.

In accordance with one aspect of this invention, there is provided a method of controlling odor emission from a toilet system in a toilet holding tank for a prolonged interval of forty-eight hours or more consisting essentially of adding to the toilet holding tank an effective amount of an additive composition that consists essentially of:

a. quaternary compound selected from a class consisting of alkyl dimethyl benzyl ammonium chloride and alkyl diethyl benzyl ammonium chloride where the alkyl moiety contains 12–18 carbon atoms, inclusive;
b. formaldyhyde; and
c. an acid buffer sufficient to buffer the additive composition in the toilet system to a pH in the range of 4–5; the effective amount being that which is sufficient to maintain a concentration of at least 100 parts per million of the additive composition throughout the prolonged interval.

In another aspect of this invention, there is provided an additive composition such as described in the method hereinbefore. In preferred embodiments, the composition is provided in pre-measured quantities to facilitate treating predetermined sizes of toilet holding tanks.

DESCRIPTION OF THE PREFERRED EMBODIMENTS

This invention may have various uses where control of odor emission from fecal matter is significant. In the following description, however, this invention will be described with respect to controlling odor emission from a toilet system in a toilet holding tank such as will be employed in the portable toilets, transportation vehicles and the like.

As noted hereinbefore, the additive composition that is employed for controlling the odor emission from the toilet system in the toilet holding tank for a prolonged interval of forty-eight hours or more consists essentially of quaternary compound, formaldehyde, and an acid buffer.

The quaternary compound is selected from the class consisting of alkyl dimethyl benzyl ammonium chloride and alkyl diethyl benzyl ammonium chloride, where the alkyl contains 12–18 carbon atoms, inclusive. As will be appreciated by those who are skilled in organic chemistry, the alkyl moieties will ordinarily be composed of even numbered carbon compounds, since the odd numbered compounds are relatively rare and much more expensive. Thus, as a practical matter, the alkyl moieties will be dodecyl, tetradecyl, hexadecyl, octadecyl, or an admixture thereof. Ordinarily, the admixture of the even numbered carbon moieties between 12 and 18 carbons, inclusive, are economical, are readily available and are employed in this invention. In fact, the n-alkyl dimethyl benzyl ammonium chlorides are commercially available from a plurality of sources; for example, available as the Hyamine (trademark of Rohm and Haas Co.) 3500, from Rohm and Haas Co., Philadelphia, Pennsylvania 19105 and as Barquat (trademark of Lonza, Inc.) MB 80 or MB 50 or an admixture thereof. The preferred composition that has been tried to date comprises an n-alkyl dimethyl benzyl ammonium chloride where the alkyl moiety is admixture of about 40 percent dodecyl ($C_{12}$), 50 percent tetradecyl ($C_{14}$), and 10 percent hexadecyl ($C_{16}$). The MB 80 is an admixture with about 20 percent ethanol and is more concentrated and therefore preferable. The MB 50 is an admixture with about 10 percent ethanol and about 40 percent water. The Hyamines from Rohm and Haas comprise about the same proportion of alkyl moieties having an average molecular weight of about 359.6 and are ordinarily supplied in a solution containing about 10 percent ethanol and about 40 percent water. The Barquat MB 80 provides excellent effectiveness and facilitates disintegration and dissolution of solids and odoriferous components.

The formaldehyde that is employed is preferably an aqueous solution. If desired, paraformaldehyde or other material that will yield formaldehyde in an aqueous solution can be employed. A variety of aqueous solutions are readily available commercially. Ordinarily, they range in the concentration of 20–40 percent by weight of formaldehyde. For example, commercial solutions of formaldehyde are available as Formalin (trademark), which contains 27 percent by weight formaldehyde in water in the U.S. and 40 percent by weight in water in the United Kingdom, and is also commercially available as a 37 percent by weight solution of formaldehyde in water. The formaldehyde acts to control odors well over the short term in and of itself but it does not retain some of the evolving basic gases in the solution. It is theorized that there may be some formaldehyde gaseous emission that helps to destroy odors in the immediate vicinity of the toilet and acts an antibacterial agent to assist in the curtailment of bacterial growth. At pH's of 5 or above, however, this invention has demonstrated that the formaldehyde and the quaternary products are not effective over a prolonged interval of forty-eight hours or more.

Accordingly, an acid buffer is employed. Any acid buffer that will buffer the solution to a pH in the range of 4–5 is effective herein. For example, phthallic acid can be employed. It has been found, however, that it is better to employ as the acid buffer potassium acid phthalate, of potassium bi-phthalate. In the concentrations employed in this invention the potassium acid phthalate establishes a pH of about 4.0 in the toilet water. As waste materials are introduced, the potassium acid phthalate changes the pH by neutralizing the more basic wastes, as well as the more acidic waste. By providing a stable pH in the range of 4–5, the potassium acid phthalate enables the retention in the solution of many volatile, obnoxious gases, such as ammonia, and resists the strongly acidic conditions that can contribute to the corrosion of metallic systems like metallic holding tanks, hinges and the like. Moreover, the acid buffer establishes a range of 4–5 for the pH such that the formaldehyde and quaternary product remain effective over a much longer interval of time, such as the prolonged interval of forty-eight hours or more.

The additive composition is added in an amount that will be effective to control the emission of noxious odors from the toilet system in the toilet holding tank. The amount that is required to be effective is that amount which will effect at least 100 parts per million residual throughout the prolonged interval; for example, forty-eight hours and more. Good initial control is achieved at application levels of 2500-3000 parts per million of the additive composition comprising the quaternary compound containing 80 percent active ingredient, formalin containing 37 percent by weight formaldehyde and potassium acid phthalate. It may be desirable to employ as much as 4000 parts per million or higher where the prolonged interval is to exceed forty-eight hours. The parts per million are stated on a basis of average in-use volume. For example, in a 20 gallon unit in which a 5-gallon initial charge was given, the average in-use volume was assumed to be 10 gallons. Expressed otherwise, the initial charge had a concentration based on 5 gallons of 5000-6000 ppm.

The concentration of the prospective ingredients may vary somewhat in the additive composition. While the inclusion of water of a known controlled hardness is preferable, the following descriptive matter gives the composition in proportions, or concentrations, based on the additive composition without water and followed with a proportion based on an additive composition including water of controlled or known hardness.

Where no water, per se, is employed in the additive composition, the additive composition should contain from 30-50 percent by weight of the quaternary compound (based on 80 percent active ingredients). The preferred concentration range is between 40-48 percent. Herein, the term "percent" is employed to signify percent by weight unless otherwise designated. Because many of the constituents are liquid, however, the percents by volume are employed. The percents by volume do not differ significantly from the percents by weight. A preferred concentration of the quaternary compound is from about 44 to about 46 percent of the additive composition.

The additive composition contains the formaldehyde in a proportion of from 30 to 50 percent by weight, based on use of an aqueous solution containing about 37 percent (Formalin) by weight formaldehyde. As with the quaternary compound, the formaldehyde is preferably employed in a concentration between 40 and 50 percent of the additive composition. A particularly preferred concentration is from about 44–48 percent Formalin in the additive composition.

The acid buffer is employed in the concentration range of from 2-15 percent by weight of the additive composition. When the potassium acid phthalate is employed, the concentration range that is preferred is from about 4 to about 12 percent by weight.

When water is employed in the additive composition, the concentrations are adjusted since, ordinarily, at least as much water is employed as there is of the quaternary or Formalin ingredients. For example, it is preferable that the additive composition have from about 20 to 40 percent of the quaternary compound, containing about 80 percent active quaternary; about 20 to 50 percent of the aqueous solution of formaldehyde containing about 37 percent by weight formaldehyde; about 1 to 10 percent by weight of the acid buffer and about 30 to 67 percent water.

The following examples are given to demonstrate the efficacy of this invention. Initial tests were made on controls that comprised aqueous solutions of fecal wastes and urine. The fecal wastes and urine controls were treated with the quaternary compound and with the Formalin. The quaternary compound that was employed was Barquat MB 80, containing 80 percent of alkyl dimethyl benzyl ammonium chloride, containing 40 percent $C_{12}$, 50 percent $C_{14}$ and 10 percent $C_{16}$ in the alkyl group, dissolved in 20 percent ethanol. The Formalin was an aqueous solution containing 37 percent by weight formaldehyde. The acid buffer was potassium acid phthalate. In the controls, good initial control was achieved at application levels of 1000 parts per million each of quaternary compound and Formalin. However, offensive odors were detected by the second day. None of the control tests proved more durable than this and were unsuccessful until the potassium acid phthalate was added to stabilize the pH in the range of 4-5.

EXAMPLE I

Into aliquot portions of the solutions of fecal wastes and urine, an application rate of 5 ounces of additive composition was added to the toilet system in the toilet holding tank in which the average in-use volume approximated ten gallons. The composition of a single application of the additive composition was as follows:

| COMPONENT | AMOUNT | CONCENTRATION percent by weight | water-free |
|---|---|---|---|
| KHP (Potassium acid phthalate) | 10 gms. (grams) | 6 | 12 |
| Formalin (37 percent by weight formaldehyde) | 38 ml. (milliliters) | 34 | 44 |
| Quaternary (Barquat MB 80) | 38 ml. (milliliters) | 24 | 44 |
| Water | 70 ml. (milliliters) | 48 | — |

Several bench tests were conducted with the above composition and excellent odor control was achieved for up to seventy-two hours. This was followed by on-line experimentation using the additive composition in a stationary vehicle equipped with a toilet holding tank system. Over a five day period, the toilet holding tank with a toilet system therein received more than 80 usages. At no time during the experiment were characteristic urine odors detectable. The only perceptable odor was attributable to about 1 milliliter of fragrance which had been added at the last minute.

Further testing included a chartered vehicle which made a five day trip and employed only one application to its holding tank. Again, no odors were detectable at any time during this trip.

EXAMPLE II

In order to reduce the application volume and likewise the shipping costs of a premixed dosage of additive composition, the water was reduced. Specifically, the additive composition was comprised of the following:

| COMPONENT | AMOUNT | CONCENTRATION percent by weight | water-free |
|---|---|---|---|
| Quaternary | 38 ml. | 31 | 46 |

-continued

| COMPONENT | AMOUNT | CONCENTRATION | |
|---|---|---|---|
| | | percent by weight | water-free |
| Formalin | 38 ml. | 31 | 46 |
| Water | 39 ml. | 32 | — |
| KHP | 6 gms. | 5 | 7 |
| Fragrance (pine scent) | 1 ml. | 1 | 1 |

Bench testing as well as on-line evaluation proved this composition to be as effective as the composition of Example I.

EXAMPLE III

In this example the acid buffer was reduced slightly. Specifically, the additive composition was comprised as follows:

| COMPONENT | AMOUNT | CONCENTRATION | |
|---|---|---|---|
| | | Percent by weight | Water-free |
| Quarternary | 38 ml. | 31 | 46 |
| Formalin | 38 ml. | 31 | 46 |
| Water | 39 ml. | 32 | — |
| KHP | 5 grams | 4 | 6 |
| Fragrance (baby powder) | 2 ml. | 2 | 2 |

Tests showed this composition equally effective in controlling odor emission. In order to remove all doubt concerning the day to day performance of the invention, an extensive on-board survey was conducted. Sample opinions were taken of commercial vehicle passengers who used the restroom facility. Four round trips were made with an average of 41 usages per trip. During one trip the toilet was used so extensively that dumping was required. Twenty-six statements were taken. Of these participants, 88 percent detected no objectionable odors in the toilet facility. Two affirmative comments concerned the dissatisfaction with the particular fragrance chosen, while the third comment referred to odors from fecal matter adhered to the bowl of the toilet. The agents observation indicated characteristic fecal or urine odors were not detectable at any time during the trip.

From the foregoing it is seen that this invention effects the objects delineated hereinbefore.

Having thus described the invention, it will be understood that such description has been given by way of illustration and example not by way of limitation, reference for the later purpose being had to the appended claims.

What is claimed is:

1. A method of controlling odor emission from a toilet system in a toilet holding tank for a prolonged interval of 48 hours and more consisting essentially of adding to the toilet holding tank an effective amount of an additive composition consisting essentially of:
  a. a quaternary compound selected from the group consisting of alkyl dimethyl benzyl ammonium chlorides and alkyl diethyl benzyl ammonium chlorides, where the alkyl group contains 12 to 18 carbon atoms, inclusive;
  b. formaldehyde; and
  c. an acid buffer in sufficient concentration to buffer said additive composition in the toilet system to a pH in the range of 4–5;
said effective amount being that which is sufficient to maintain a concentration of at least one hundred parts per million of said additive composition throughout the prolonged interval.

2. The method of claim 1 wherein said effective amount of said additive composition is 2500–3000 parts per million, based on the average in-use volume of said holding tank.

3. The method of claim 1 wherein said effective amount of said additive composition is 5000–6000 parts per million, based on the initial charge.

4. The method of claim 1 wherein an amount of said additive composition is employed that is sufficient to effect initially at least one thousand parts per million in said toilet system in said toilet holding tank.

5. The method of claim 4, wherein said formaldehyde is employed in liquid form comprising an aqueous solution of from 20–40 percent weight formaldehyde and said additive composition is employed in a proportion as follows: in a ten-gallon toilet holding tank, 20–40 grams of quaternary compound, comprising 80 percent active ingredient, 30–50 milliliters liquid form formaldehyde and 2–20 grams acid buffer.

6. The method of claim 1 wherein said additive composition is initially present in an amount of at least one thousand parts per million; and said additive composition comprises 20–40 percent by weight of said quaternary compound, 20–50 percent by weight of an aqueous solution containing 20–40 percent by weight of formaldehyde, 1–10 percent by weight of acid buffer and 30–67 percent by weight water.

7. The method of claim 6 wherein said acid buffer is potassium acid phthalate and said quaternary compound is an alkyl dimethyl benzyl ammonium chloride, where said alkyl group comprises a mixture of groups having about 40 percent containing 12 carbon atoms, about 50 percent containing 14 carbon atoms, about 10 percent containing 16 carbon atoms.

8. An additive composition consisting essentially of ingredients for controlling odors in a toilet system in a holding tank consisting essentially of a quaternary compound selected from the group consisting of alkyl dimethyl benzyl ammonium chlorides and alkyl diethyl benzyl ammonium chlorides, where the alkyl group contains 12–18 carbon atoms, inclusive; formaldehyde; and an acid buffer sufficient to buffer said additive composition in the toilet system to a pH in the range of 4–5, the concentration of acid buffer being at least one percent by weight of said additive composition.

9. The additive composition of claim 8 wherein said additive composition is in a pre-measured amount and contains 20–40 grams of said quaternary compound; 30–50 milliliters of an aqueous solution containing 20–40 percent by weight of formaldehyde; 2–20 grams of potassium acid phthalate and 30–100 milliliters of water; said amount being predetermined for a ten gallon toilet holding tank.

10. The additive composition of claim 8 wherein said quaternary compound is an alkyl dimethyl benzyl ammonium chloride, where said alkyl group comprises an admixture of alkyl moieties containing about 40 percent of a moiety having 12 carbon atoms, about 50 percent of a moiety having 14 carbon atoms, and about 10 percent of a moiety having 16 carbon atoms in an ethanol solution containing about 20 percent by volume ethanol; said acid buffer is potassium acid phthalate and said additive composition contains water in a proportion of about 30–67 percent by volume.

11. The composition of claim 10 wherein said additive composition contains about 20–40 percent by weight quaternary compound; about 20–50 percent by volume aqueous solution containing about 37 percent by weight formaldehyde; 1–10 percent by weight potassium acid phthalate.

* * * * *